United States Patent
Vorm

(10) Patent No.: US 8,613,216 B2
(45) Date of Patent: Dec. 24, 2013

(54) DYNAMIC THERMAL FOCUSING OF CHROMATOGRAPHIC SEPARATIONS

(75) Inventor: Ole Vorm, Odense M (DK)

(73) Assignee: Proxeon Biosystems A/S, Odense C (DK)

( * ) Notice: Subject to any disclaimer, the term of this patent is extended or adjusted under 35 U.S.C. 154(b) by 396 days.

(21) Appl. No.: 13/128,611

(22) PCT Filed: Nov. 12, 2009

(86) PCT No.: PCT/EP2009/065041
§ 371 (c)(1),
(2), (4) Date: Jun. 3, 2011

(87) PCT Pub. No.: WO2010/057826
PCT Pub. Date: May 27, 2010

(65) Prior Publication Data
US 2011/0252873 A1   Oct. 20, 2011

Related U.S. Application Data

(60) Provisional application No. 61/116,323, filed on Nov. 20, 2008.

(51) Int. Cl.
  *G01N 3/08*    (2006.01)
(52) U.S. Cl.
  USPC ........................................................ 73/61.53
(58) Field of Classification Search
  USPC .................... 73/61.52, 61.53, 61.55
  See application file for complete search history.

(56) References Cited

U.S. PATENT DOCUMENTS

| 4,404,845 | A | | 9/1983 | Schrenker |
| 4,715,217 | A | * | 12/1987 | Coyne et al. ................ 73/61.55 |
| 5,547,497 | A | * | 8/1996 | Klemp et al. ................ 96/104 |
| 5,691,206 | A | * | 11/1997 | Pawliszyn ................ 436/178 |
| 6,042,787 | A | * | 3/2000 | Pawliszyn ................ 422/69 |
| 6,537,827 | B1 | * | 3/2003 | Pawliszyn ................ 436/178 |
| 2007/0181702 | A1 | * | 8/2007 | Ziegler ................ 237/19 |
| 2009/0158820 | A1 | * | 6/2009 | Bostrom et al. ............ 73/61.53 |

FOREIGN PATENT DOCUMENTS

| DE | 85 36 810 | 11/1986 |
| EP | 0 438 618 A1 | 7/1991 |
| EP | 0 716 302 A2 | 6/1996 |
| EP | 1 876 453 A1 | 1/2008 |
| WO | WO 98/21574 | 5/1998 |

OTHER PUBLICATIONS

Holm et al., "Novel column oven concept for cold spot large volume sample enrichment in high throughput temperature gradient capillary liquid chromatography," *J. Sep. Sci.* (2003) 26: 1147-1153. XP-002567277.

Molander et al., "Temperature-promoted large-volume solute enrichment in column-switching miniaturized liquid chromatography: Determination of an antioxidant," *Analyst* (2002) 127: 892-897. XP-002567278.

* cited by examiner

*Primary Examiner* — John Fitzgerald
(74) *Attorney, Agent, or Firm* — Merchant & Gould P.C.

(57) ABSTRACT

There is provided a method for thermally focusing the elution times of compounds of a liquid chromatography system comprising a pre-column and a separation column as well as to provide a liquid chromatography system, wherein the chromatographic separation of a mixture of substances is optimized.

10 Claims, 6 Drawing Sheets

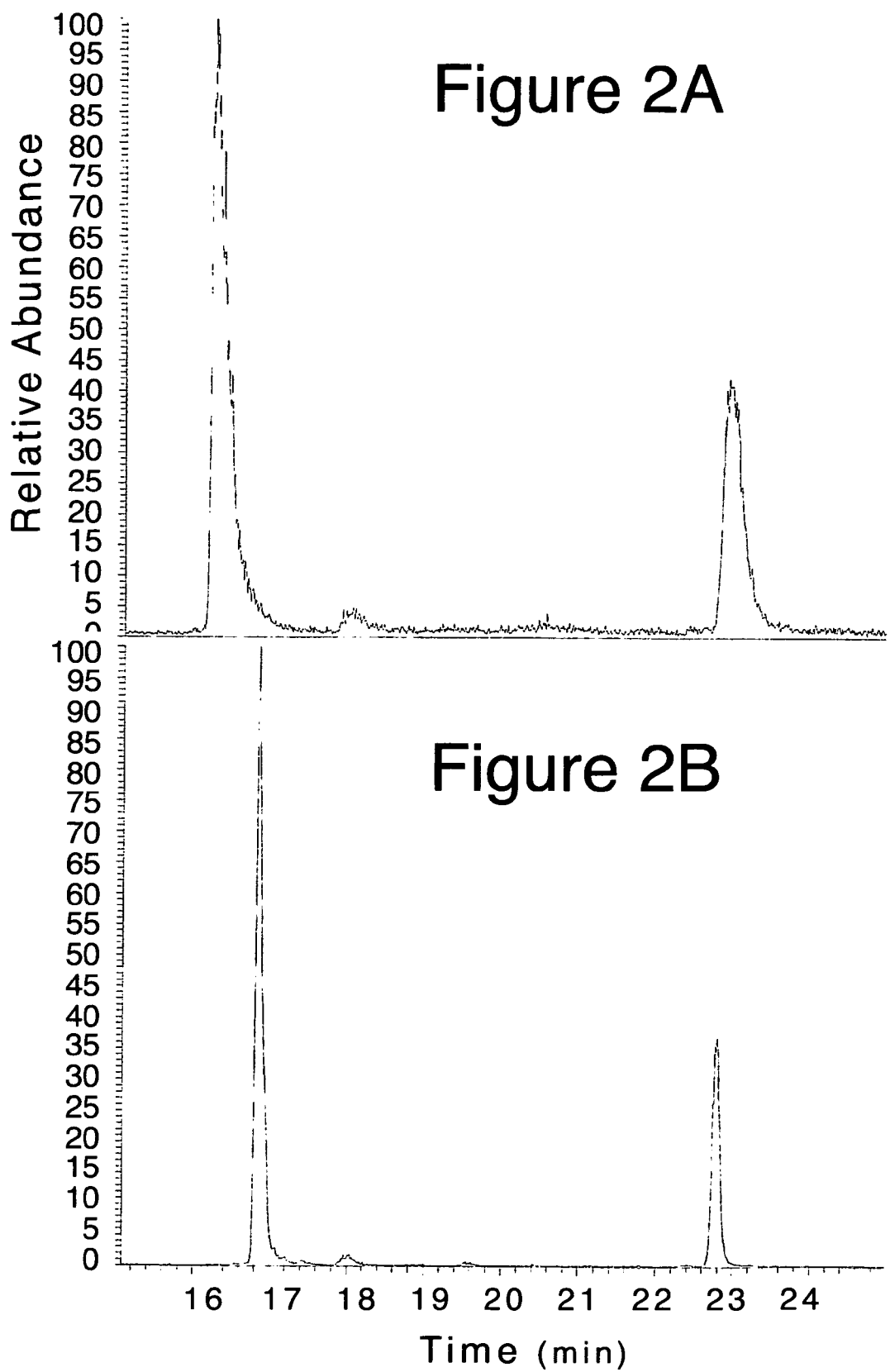

DYNAMIC THERMAL FOCUSING OF CHROMATOGRAPHIC SEPARATIONS

This application is a National Stage Application of PCT/EP2009/065041, filed 12 Nov. 2009, which claims benefit of Ser. No. 61/116,323, filed 20 Nov. 2008 in the United States of America and which applications are incorporated herein by reference. To the extent appropriate, a claim of priority is made to each of the above disclosed applications.

FIELD OF THE INVENTION

The present invention relates to a liquid chromatography system and a method for focusing the chromatographic separation on one, two, or more columns of a liquid chromatography system by dynamically and differentially adjusting the temperatures of different segments of the liquid transfer lines and the solid phases of the setup. More specifically, the invention primarily relates to a method for thermally focusing the eluting compounds of a pre-column and a separation column of a liquid chromatography system.

BACKGROUND OF THE INVENTION

Detection efficiency by means of electrospray mass spectrometry is concentration dependent so the best sensitivity is achieved when samples are eluted in volumes that are as small as possible. This is done by using chromatographic columns of narrow inner diameters and low flow rates for the mobile phase. However, small column volumes provide fewer binding sites on the stationary phase such that the loading capacity is low. Overloading columns with sample results in poor resolving power, broad and asymmetric peaks and eventually deteriorating detection efficiency.

In liquid chromatography, the equilibrium distribution between analyte that is immobilized on the stationary phase and analyte dissolved in the mobile phase is a function primarily of the compositions of the mobile and stationary phases but also many other physical/chemical parameters may have a pronounced effect. One such parameter is temperature and it is common practice to use column ovens (and more rarely column-coolers) in order to maintain a stable temperature of the columns during analysis since temperature stability greatly enhances the retention time reproducibility of repeat experiments. In addition, it is often observed that eluting peaks are slightly narrower and more symmetrical when column temperatures are raised slightly above ambient temperature. Typical temperature ranges used for separation columns are 30-50° C. In nano-LC (which is liquid chromatography that uses a flow range of typically 50 nL/min to 500 nL/min) and in proteomics applications in particular, the use of column temperature control is less common than in most other application areas and when using larger flow ranges.

Frequently, trapping columns (or "pre-columns") are used to capture samples during sample loading where such trap-columns are shorter and often of slightly wider ID than the analytical (or "separating") columns. By virtue of being shorter and wider, the flow rate through pre-columns when loading and desalting samples can be much higher than when samples are applied directly onto analytical columns. This saves analysis time. Compounds eluted from the pre-column move onto the analytical column and are separated there. A primary negative effect caused by the combined use of trapping columns in-line with separating columns, is that peak widths are much (typically 1.3 to 5 times) wider than when samples are loaded directly onto separating columns (entirely omitting trap-columns). This reduces resolving power and absolute sensitivity. Typically the ID for trap columns is in the range of 100% to 130% of the ID of the separating columns and lengths of trap columns are typically from 0.5 cm to few centimeters whereas the lengths of separating columns typically range from 5 cm to 100 cm. The larger the trapping column ID (and hence volume) is, the more pronounced will the peak broadening effect typically be.

Currently, experimental conditions for LC-MS in proteomics are chosen to match the requirements for sensitivity, analysis speed, dynamic range, and resolution. Each of these parameters is highly important and much effort goes into finding ways to improve and optimize these parameters, albeit, one cannot optimize all parameters simultaneously because of counteracting effects.

The chromatographic retention and resolution, i.e., the separation of the different peaks in the chromatogram associated with different substances, are to some extent influenced by the system temperature. It is known that the system temperature can be manipulated to optimise conditions for a specific separation task. And it is widely practised to ensure reproducible chromatographic results, by holding the temperature constant during the separation process and from analysis to analysis. To this end, a thermally stabilized housing is often employed in liquid chromatography in order to keep the chromatographic bed temperature in the separation column constant. By adjusting temperatures, it is also possible to optimize the separation performance of a separation column for a given analyte and given set of mobile phases. Various forms of thermally stabilized housings of the cited type are known, in which the temperature within the housing is essentially constant, such as a water bath, circulating-air heating/cooling, a heating jacket, etc.

The prior art includes various apparatus for thermal stabilization in liquid chromatography.

U.S. Pat. No. 4,404,845 discloses a thermal regulator for liquid chromatographs. This regulator comprises a thermostat arrangement for the mobile phase and the separation column in a liquid chromatograph, whereby the thermostat has a heat transformer through which the mobile phase passes. The heat transformer comprises a heating and/or a cooling element and is positioned between a sample injection device and the inlet of the separation column. The heat exchanger serves to selectively heat or cool the ambient air surrounding the separation column. Thermal regulation of the mobile phase and the separation column prevents disadvantageous temperature gradients.

DE8536810 discloses an oven for setting the temperature of separation columns for high pressure liquid chromatography. In order to avoid a fluctuation of the retention times due to temperature deviations, temperature regulation of the separation column is proposed. The temperature of the separation column in this case is set by an oven consisting of a thermally heatable and coolable block of a metal with high thermal conductivity and with a well for accepting one or more separation columns. A Peltier element is arranged on the heatable and coolable block to allow working temperatures to be set below room temperature.

EP438618 discloses an apparatus for thermally stabilizing a mobile phase in a liquid chromatograph. This apparatus comprises a chromatographic column to which an ingoing capillary tube and an outgoing capillary tube are attached, this chromatographic column being positioned in a receptacle element that can be adjusted to a desired temperature using a temperature control unit. In order to avoid excessive temperature of the liquid directed to a detector through the outgoing capillary tube, which would lead to inaccurate measurement, it is proposed in this case to route the ingoing and outgoing capillary tubes parallel with one another for a predefined distance in order to achieve a heat exchange between the higher-temperature capillary tube leading to the detector and the lower-temperature ingoing capillary tube leading to the separation column.

In addition to the aforementioned apparatus with one separation column, there are known liquid chromatography systems that work with two columns, a pre-column and a separation column. In transferring the substances to be analyzed from the pre-column to the separation column, however, a more strongly elutropic eluent is required for the pre-column than for the separation column, even if the same packing material is used in both columns. This causes the dispersion in the pre-column to act as an "elutropic injection volume", whereby even well-packed pre-columns considerably reduce the overall efficiency of the liquid chromatography system. Of added disadvantage in this case are pre-columns with low efficiency and high capacity.

SUMMARY OF THE INVENTION

In view of the prior art, it is an object of the present invention to provide a method for thermally focusing the elution times of compounds of a liquid chromatography system comprising a pre-column and a separation column as well as to provide a liquid chromatography system, wherein the chromatographic separation of a mixture of substances is optimized. This object is met by a method and by a liquid chromatography system in accordance with the present invention. The invention will hereinafter be referred to as "Thermal Focusing" (TF) with additional discrimination between "Dynamic" Thermal Focusing (DTF) and "Static" Thermal Focusing (STF), where DTF offers significant advantages over STF.

The principle of TF utilizes the abovementioned common phenomenon that the distribution of immobilized versus free analyte is a function of temperature. But rather than simply keeping column temperatures constant it has been found beneficial to use temperatures that are vastly different at the location of the pre-column (trap-column) and the location of the separating-column (STF), and change temperatures at both of these locations over the course of a chromatographic analysis (DTF).

Specifically, TF utilizes a steep temperature gradient between a trap column and a separating column in order to focus analytes that elute off of the trap column into a narrow band at the very beginning of or through the separating column. This focusing effect is, by example, very prominent for peptides, using the same or related stationary phase materials in both columns but where the trap column is kept at, say 50° C., and where at least the initial part of the separating column is kept at a lower temperature, e.g. 0° C. The separating column cooling preferably includes also a portion of the transfer tubing coming from the trap column such that mobile phase is cooled before reaching the separating column. Similarly, the tubing leading into the trap-column should also be temperature controlled such that buffers have reached the set trap-column temperature already before physically reaching the front end of the trap-column. The cooled area of the separating column need not cover the entire length of the separating column whereas the entire length of the trap column preferably should be of uniform temperature.

The focusing effect increases with the size of the temperature drop. The cause of the focusing effect is that analytes released at high temperatures from the pre-column at a given point (T1) in a mobile phase gradient will, when cooled before the separating column, strongly displace from the mobile phase to the stationary phase and be immobilized until such later point in time (T2) when the gradient has changed sufficiently to again facilitate elution. By controlling parameters such as flow rates and gradient steepness, it is possible for many given combinations of mobile and stationary phases, to create conditions that will focus analytes eluting off of the trap column into much narrower bands on the separating column. This requires only that the elution volume for each analyte when eluting from the trap-column be smaller than the volume of mobile phase that flows between the columns during the time from T1 to T2.

For gradients of practical and typical duration, TF allows the matching of very large ID trap columns with narrow ID separating column without significant peak broadening effects.

Studies performed by the present inventors indicate that the ID of the trap column can be e.g. 500% of the ID of the separating column while the length of the trap column may also be longer than normal without leading to detrimental peak broadening. This translates into much improved loading capacity (as this is proportional to trap column volume) of the entire system and higher loading and de-salting speeds (as this is roughly proportional to the column radius to the fourth power and only inversely proportional to the column length). In practice, for complex samples, this can provide one to two orders of magnitude higher dynamic range and/or sensitivity of nano-LC-MS experiments. With the larger diameter, pre-columns are also less likely to be blocked by particulate matter and debris contained in liquid samples and hence the overall nano-LC analysis becomes more robust than it is with the currently used, relatively narrow diameter pre-columns.

Since analytes are released from the trap column and "snap" onto the separating column in narrow bands, the resolution of peaks observed when using TF and a trap/separating column setup is often just as good and sometimes even better than the resolution observed when samples are loaded directly onto a separating column with current approaches (omitting the use of a trap-column altogether).

The combination of these effects means that TF makes it possible to simultaneously achieve significantly higher loading speeds, sensitivity, robustness, and/or dynamic range than what is achieved with state-of-the-art approaches today while maintaining the same resolving power.

An additional positive effect of the temperature controls of both columns with TF is that the retention time reproducibility remains high despite changes in sample loads and the concentration of impurities (salt-load) from sample to sample.

Also, TF generally alleviates the peak broadening caused by diffusion and turbulence in large void volumes in-between the trap and the separating columns. Such void-volume issues are frequently the result of imperfect connections between columns, fittings, and tubing where such imperfections cause "dead-volumes" (that are unswept) and perturb the fluid flow in a manner that causes peak broadening. When using TF, essentially only dead volumes and perturbations lying after the separating column will lead to peak broadening, thus the technique is more forgiving than current approaches where there slightest imperfection can lead to large peak broadening effects and therefore reduced sensitivity. When using columns and tubing with inner diameters below 150 µm and flow rates below 1 µL/min this beneficial effect of TF becomes important also for expert users since even small dead volumes and perturbations will have pronounced detrimental effects to the chromatography, resulting in broad and asymmetric peaks.

Using TF in static mode (STF) has two major drawbacks:
1) When loading samples onto a trap column that is kept at elevated temperatures, some analytes may not bind efficiently, and e.g. some very hydrophilic components may flow straight through the trap column and escape analysis. To avoid this loss of some analyte species, it is an advantage to keep the trapping column at low temperatures, e.g. 0° C., while loading and desalting samples and then only raise trap column temperatures when the gradient elution is to begin. This actually often helps bind more analytes than one observes when loading samples at ambient temperatures as is mostly done with current nano-LC-MS approaches.
2) Conversely, the cooled separating column can bind certain analytes and impurities (such as detergents and polymers) so strongly that these remain immobilized on the column throughout the entire gradient, even during its latter part which is usually devised to help clean the separating column prior to next sample being analyzed. This will lead to accumulation of analytes and impurities on the column such that the column may be rendered useless or performing badly after only few sample injections. To avoid this loss of separating power, it is an advantage to raise the temperature of the separating column to at least the same temperature as that of the trap column towards the very last part of the gradient, such that every molecular species that is transferred from the trap to the separating column will also be washed out of the separating column for each analysis cycle.

When including these temperature changes over time, TF should be referred to as DTF which has the just mentioned significant advantages over STF.

Focusing effects have previously been achieved and is commonly used in chromatography by carefully matching different stationary phases in trap and separating columns. This approach is often cumbersome and normally only helps focus few select compounds and not a broader group of compounds. In addition, unwanted negative effects such as specificity switches (resulting in split peaks) may be observed. TF is simpler to deploy and control and focuses over broad ranges of compounds simultaneously. It is however possible to achieve even further optimized separation effects by coupling the use of TF with the matching of different trap and separating column materials.

Thus it is an object of the present invention to provide a method for thermally focusing analytes to be analysed by virtue of a pre-column and a separation column for liquid chromatography, as well as to provide a liquid chromatography system, in which the separation efficiency of the liquid chromatography system is augmented and not impaired by the pre-column. This object is met by a method and by a liquid chromatography system in accordance with the appending claims.

According to an embodiment of the present invention, a method is provided for thermally stabilizing a liquid chromatography system with the following steps: operation of the pre-column, during an enrichment phase for enriching a sample in the pre-column, at a first temperature lower than an operating temperature of the separation column; heating the sample contained in the pre-column, after completion of the enrichment phase, to a second temperature that is higher than the operating temperature of the separation column; initiating a gradient elution of the separation column while transferring the sample contained in the pre-column to the separation column; and cooling of the sample to the operating temperature of the separation column, wherein the second temperature of the pre-column is typically at least 40° C. higher than the operating temperature of the separation column. Finally the temperature of the separating column may be raised to at least the same temperature as that of the trap column towards the very last part of the gradient, such that every molecular species that is transferred from the trap to the separating column will also be washed out of the separating column for each analysis cycle.

In the enrichment process of the invention, which employs a pre-column, the pre-column is operated at a lower temperature than the analytical (separation) column. As a result, the break-through of early eluting substances can be reduced or prevented.

The present invention may further increase the capacity of the pre-column by using an ID of the pre-column that is from 100% to 500%, preferably from 120% to 350%, more preferably from 130% to 200%, and most preferably from 150% to 170% of the ID of the separating column while the length of the trap column is from 1% to 300%, preferably from 10% to 150%, more preferably from 60% to 120%, and most preferably from 70% to 100% of the length of the separating column.

The present invention, moreover, provides a liquid chromatography system with a pre-column for enriching a sample; a separation column with a fluid-transfer link to the pre-column; a first heat exchanger device arranged on the pre-column and enabling independent control of the pre-column temperature; a second heat exchanger device arranged on the first between 5% and 20%, preferably 30%, more preferably 40%, and most preferably at least 50% of the length of the separation column enabling independent control of the temperature of the first part of the separation column; and occasionally a third heat exchanger device arranged on the rest of the separation column enabling independent control of the temperature of this part of the separation column.

The present invention provides, in an advantageous manner, a physical and electrical de-coupling of the heat exchangers of the pre- and separation columns of a liquid chromatography system, so that two columns, namely the pre-column and the separation column as well as the first part of the separation column, can be operated at different temperatures, resulting in the ability to optimize the selectivity and/or separation efficiency.

BRIEF DESCRIPTION OF THE DRAWINGS

The following describes in greater detail preferred embodiments of the present invention with reference to the accompanying drawings, in which FIG. 1A shows the thermo-element used for heating and cooling of the separation column, in this case, a Peltier element in contact with an elongated block of aluminium that has a groove which precisely fits around the column (Ø360 µm). The aluminium piece is surrounded by an insulator layer made of plastic and foam in order to minimize the amount of energy exchanged with the ambient air (please note the lid is shown in exploded view). FIG. 1B similarly shows the thermo-element used for heating and cooling of the pre-column. This is also an aluminium block with grooves cut for a precise fit to the pre-column. Also the connection fitting and some of the tubing upstream of the pre-column (i.e. towards the LC system) is enclosed in the thermo-element to ensure that the liquid (and sample) has reached the desired temperature by the time it reaches the front edge of the pre-column. The cooling and heating events are more time critical for the pre-column than for the analytical column and also the system must be able to cool/heat pre-columns of significantly wider diameter (than the separation columns have) and therefore this thermo-element was made with two larger Peltier elements and a substantially larger heat sink. FIG. 1C shows both thermo-elements relative to one another where the pre- and separation-columns have been connected by a piece of transfer tubing, preferably of low inner diameter, in this case 25 μm ID.

FIG. 2 compares chromatograms taken with the chromatography system of the present invention without (top pane) and with (bottom pane) thermal focusing. Both chromatograms were recorded with otherwise identical experimental parameters. The sample loaded was a tryptic digest of BSA (bovine serum albumin, Mw 66 kDal) and the ion trace is displayed for two values of mass-to-charge ratios, namely the peptides eluting to give rise to ions of m/z 722.6 and 582.5, resp. The separation column used had an inner diameter of 75 μm and a length of 8 cm and hence its volume was approximately 112 nL. The pre-column and an artificially introduced dead-volume immediately before the separation column were approximately 2050 nL, i.e. a volume that is around 18 times larger than that of the separation column. The upper chromatogram shows the envelope of the peaks eluting under normal running conditions, that is without thermal focusing turned on. Both of the two peaks are around 40 seconds wide at the intensity level of 5% above baseline. Also both peaks exhibit pronounced asymmetry. The lower chromatogram shows the same experiment albeit with thermal focusing turned on. The two peaks have now been focused such that they have become significantly more symmetrical and the peak widths at 5% above base line has dropped to around 12 seconds. As a result of the narrower peaks, the signal intensity is almost 3 times higher and the general signal-to-noise-ration of the entire chromatogram has improved.

DETAILED DESCRIPTION OF THE INVENTION

Figure 1A:
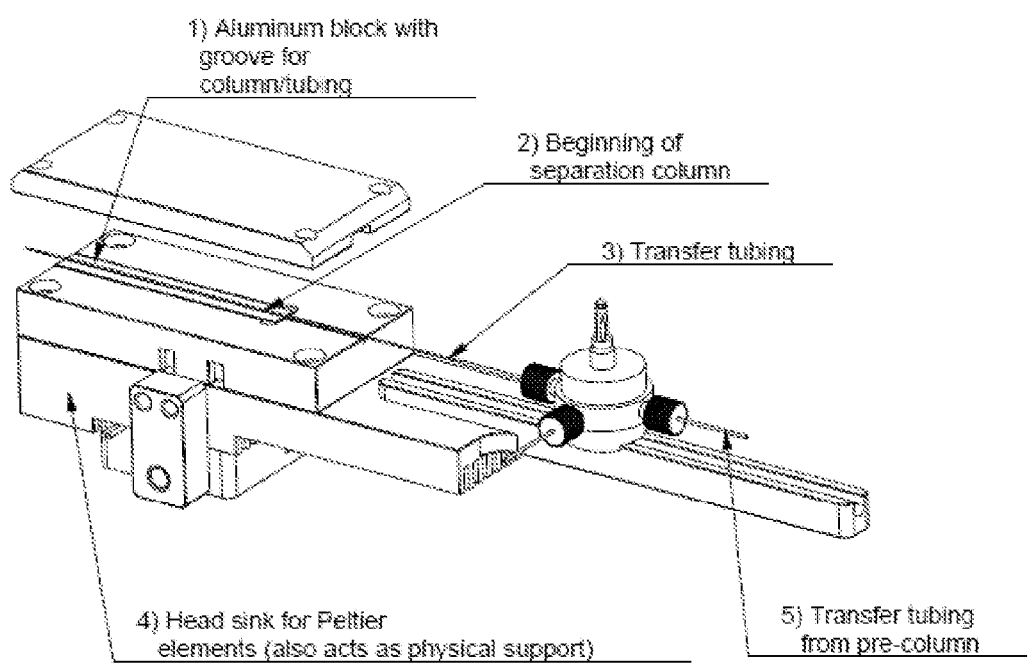
FIGS. 1A to 1C show a first embodiment of the cooling/heating devices required for a liquid chromatography system in accordance with the present invention.
Figure 1B:
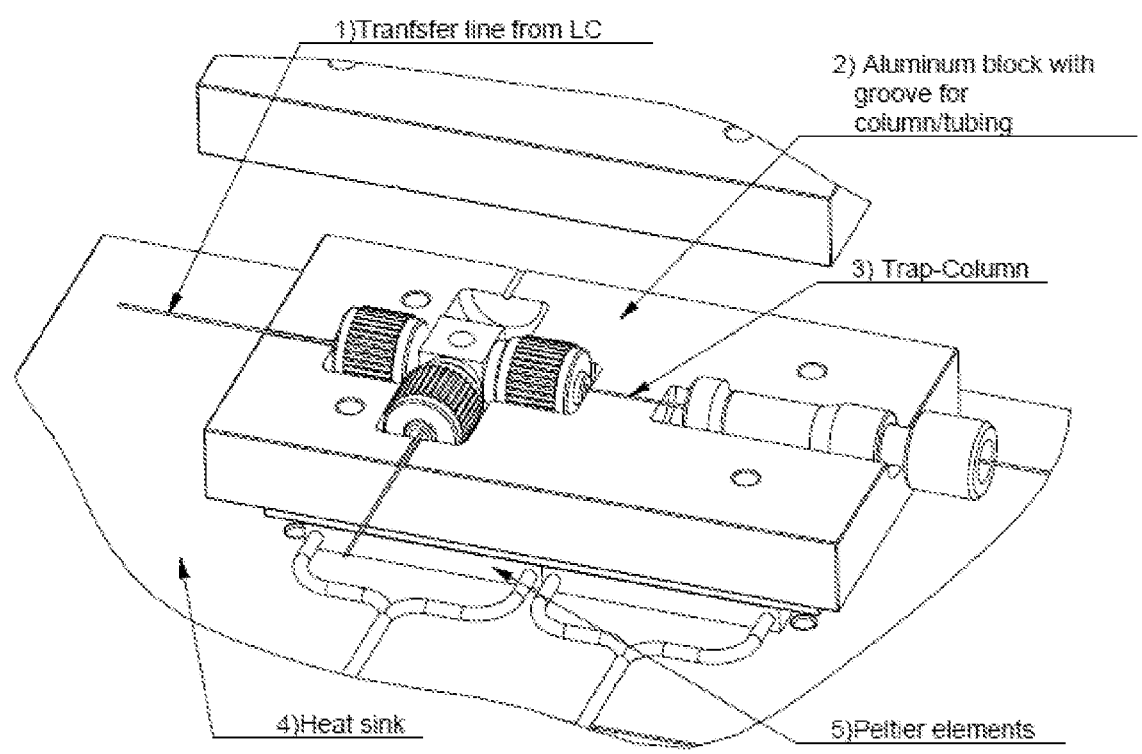
Figure 1C:
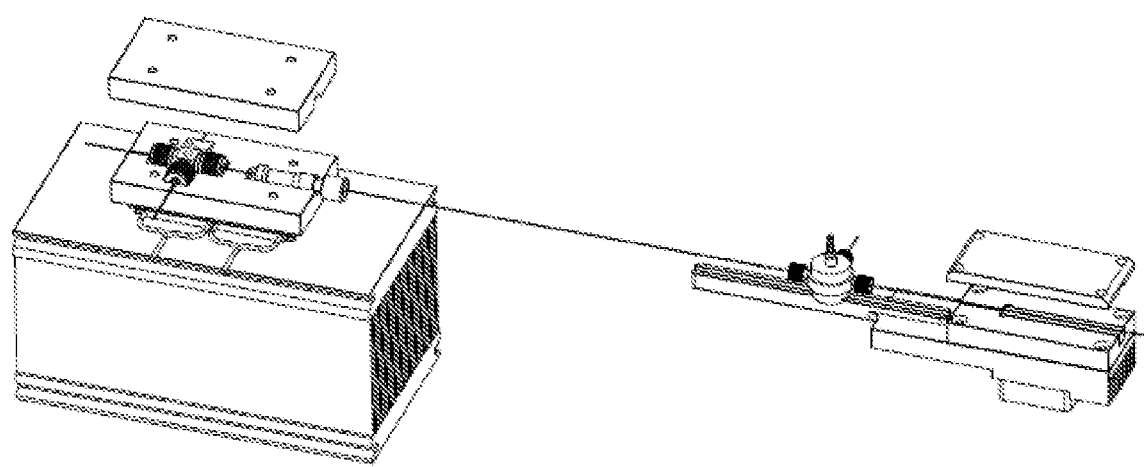

The following describes in greater detail preferred embodiments of the present invention with reference to the accompanying drawings, in which FIGS. 1A to 1C show a first embodiment of the cooling/heating devices required for a liquid chromatography system in accordance with the present invention. FIG. 1A shows the thermo-element used for heating and cooling of the separation column, in this case, a Peltier element in contact with an elongated block of aluminium that has a groove which precisely fits around the column (Ø360 μm). The aluminium piece is surrounded by an insulator layer made of plastic and foam in order to minimize the amount of energy exchanged with the ambient air (please note the lid is shown in exploded view). FIG. 1B similarly shows the thermo-element used for heating and cooling of the pre-column. This is also an aluminium block with grooves cut for a precise fit to the pre-column. Also the connection fitting and some of the tubing upstream of the pre-column (i.e. towards the LC system) is enclosed in the thermo-element to ensure that the liquid (and sample) has reached the desired temperature by the time it reaches the front edge of the pre-column. The cooling and heating events are more time critical for the pre-column than for the analytical column and also the system must be able to cool/heat pre-columns of significantly wider diameter (than the separation columns have) and therefore this thermo-element was made with two larger Peltier elements and a substantially larger heat sink. FIG. 1C shows both thermo-elements relative to one another where the pre- and separation-columns have been connected by a piece of transfer tubing, preferably of low inner diameter, in this case 25 μm ID.

Figure 3:
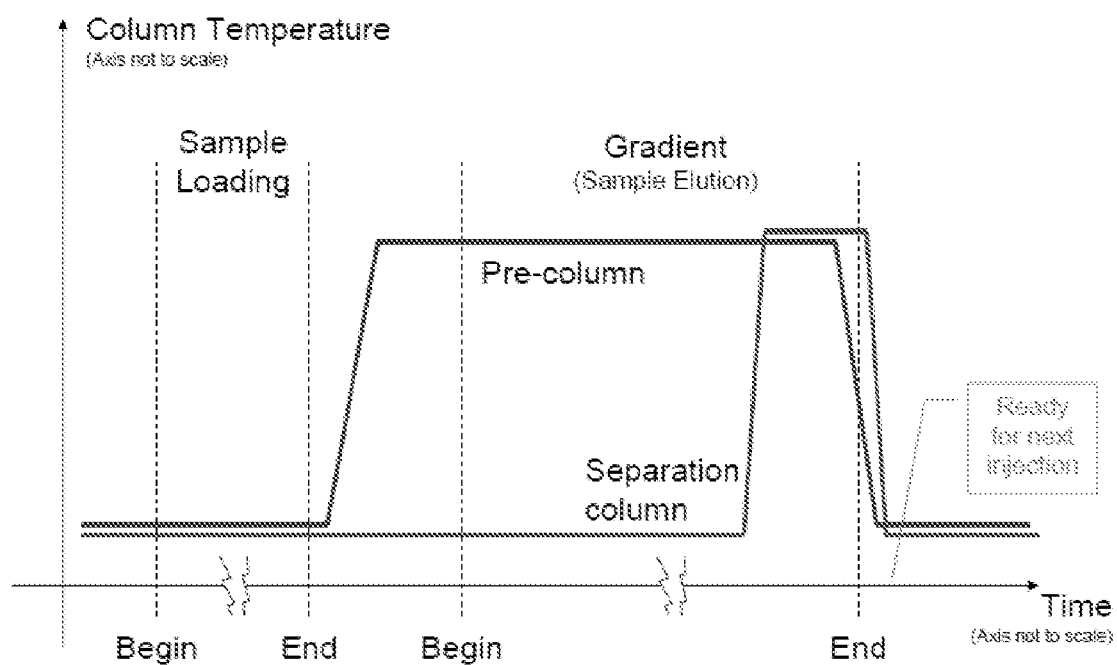
FIG. 3 shows a schematic representation of the temperatures of the pre-column and the separation-column as a function of time during a chromatographic analysis that uses DTF. The two temperature extrema need not be the same or even near the same for the two columns as the figure might imply. Neither axis is drawn to scale. When using ultra-fast gradients or working with particularly sticky compounds, it is also conceivable that the separation-column temperature must be held at "high" for longer time than for the pre-column. But for most analyses, the separation column temperature is only raised for a relatively short period of the overall cycle.

The invention has been implemented and tested for the use in nano-LC-MS. The implementation deploys Peltier cooling/heating elements with aluminum heat sink and fan. Peltier elements heat small aluminum bars that are covered with isolating foam. Temperature sensors and computer controlled feedback regulation is used to regulate temperatures within margins of less than one degree from the set-point except during the rapid transitions between alternating temperatures in the DTF cycle. Synchronization with the LC analysis cycle (specifically, the sample loading and de-salting and gradient formation) ensures that DTF benefits are optimized (see also FIG. 3).

In the nano-LC regime of flow rates of 0.01 to 500 nL/min, and with transfer tubing and column diameters of a few to few hundred μm it is straightforward to drain or add the necessary amount of heat on the required time-scale. Peltier elements are in most regards ideal for the application but other alternative means of providing the energy transfer could include liquid baths, air contact (ovens/freezers), depressurizing/compressing gasses, heating coils etc. In particular it may be an advantage to use such other means of creating the heat transfer when TF is implemented in chromatographic systems that use larger flows and therefore require more heat to be transferred within a given period of time.

FIGS. 1A-C show a liquid chromatography system in which a pre-column for enriching the sample and a separation column are arranged (and which may include collective or discrete housings (not shown)). In order to operate pre-column and separation columns at three different, constant temperatures, heat exchangers (and possibly their housings) are arranged spatially separated from one another. First heat exchanger is associated with the pre-column, and second and third heat exchangers are associated with the separation column. The sample is loaded onto the pre-column e.g. by means of an LC pump via an inlet transfer tube. The outlet of the separation column is connected to a detector (not shown).

The arrangement shown in FIGS. 1 permits three different temperature environments to be realized. In order to create these temperature environments, heat exchangers are connected to a control unit that enables independent control of the pre-column temperature and/or the separation column temperatures.

The design of the liquid chromatography system shown in FIGS. 1 allows, during the enrichment phase, operation of the pre-column at a temperature lower than the its operating temperature during gradient elution.

After the enrichment phase, the pre-column and thereby the sample contained therein is heated to a second temperature at least 10° C. higher and typically 40° C. higher than the operating temperature of the separation column. As a result, the substances being analyzed in the sample elute in a gradient at a solvent composition that is less elutropic compared to the solvent composition required for prior art liquid chromatography systems with a pre-column is transferred from the pre-column to the separation column.

The sample now passes through a second heat exchanger, is cooled to the operating temperature of the first part of the separation column, and adsorbs to the stationary phase and thereby becomes concentrated again early in the separation column. Finally, the sample passes through a third heat exchanger (or a not-cooled portion of the separation column) and then elutes from the separation column. In a preferred embodiment the operating temperature of the separation column is 0° C., while the second temperature of the pre-column is 50° C.

Using the liquid chromatography system and method of the invention, the band widening occurring in prior art liquid chromatography systems with a pre-column, caused by the pre-column and the connecting fittings and capillary tubes, is prevented for the most part, resulting in an increase in the separation efficiency of the liquid chromatography system.

The following describes an example of an analysis that demonstrates the principle and effect of the invention, with reference to FIG. 2 where the upper pane shows a chromatogram recorded without TF and the lower pane shows a chromatogram with DTF active.

The experiment used an in-house packed pre-column of inner diameter 150 μm and length of around 1 cm, packed with C18 reverse phase material (5 μm bead size, ReproSil PurA, 120 Å pore size, Manufacturer: Dr. Maisch, Ammerbuch-Entringen, Germany). This was connected to a 10 cm long piece of empty tubing of ID 500 μm, which corresponds to a volume of 2 μL, in order to demonstrate the effect a dead-volume or a larger pre-column has. Following this empty tubing came an in-house packed separation column of inner diameter 75 μm and length of around 8 cm, packed with C18 reverse phase material (3 μm bead size, ReproSil PurA, 120 Å pore size, Manufacturer: Dr. Maisch, Ammerbuch-Entringen, Germany).

The sample (analyte) loaded to record each of the two chromatograms was 100 fmol of peptides from bovine serum albumin that had been digested with trysin. Whereas peptides were recorded over a wide mass-to-charge range, FIG. 2 displays selectively only two peptides (at nominal m/z 582 and 722, resp.). The chromatograms were recorded by an LCQ Classic ion-trap mass spectrometer (ThermoFisher Scientific, San Jose, Calif., USA).

The chromatography system used was an Easy-nLC from Proxeon Biosystems A/S, Odense, Denmark. The A-buffer used was: 5% acetonitrile and 0.1% formic acid in water; and the B-buffer used was: 20% water and 0.1% formic acid in acetonitrile. The gradient was from 0% B to 35% B in 25 minutes.

In the experiment without TF, both pre-column and separation column were at ambient temperature of around 23 degrees centigrade whereas the experiment with DTF maintained a temperature of the pre-column of 40 degrees centigrade and a separation column temperature of 0 degrees centigrade during the gradient elution.

The focusing is readily visible inasmuch as the elution envelope of both peptide peaks become nearly three times narrower and the intensity of each peak thus becomes nearly three times higher.

In the following, further details regarding the heat exchanger in accordance with the present invention will be explained. In a preferred embodiment of the invention, the first, second, and third heat exchanger devices are thermally decoupled, but still arranged in the same column housing, without a partition between the heat exchanger devices. The first, second, and third heat exchanger devices can be heated or cooled independently of each other with equal or with different temperatures. A feature contributing to the thermal decoupling of the first and second heat exchanger devices is that there is no circulation of air in the column housing so that the first and second heat exchanger devices, due to their spacing and orientation, can hardly exchange heat, even if they are arranged in the same column housing.

The heat exchanger devices in a preferred embodiment of the invention are characterized by a material having good heat conducting properties, by thermally well integrated fluid capillaries for pre-thermostating of the solvent/sample mixture, and by ribs for receiving the column and for heat transfer thereto. The heat exchanger devices can be heated and cooled in a controlled way. The heat transport for thermal control of the separation column is accomplished via the solvent in the tubing prior to the column, via the contact between the separation column and the heat exchanger and via heat radiation and convection between the ribs supporting the separation column.

As compared to circulating air, the described solution has the advantage that different temperature settings of the first and second heat exchanger devices are possible without negative thermal influences between these devices, even if they are arranged in the same column housing. It is an advantage of the controlled sample pre-thermostating that radial and longitudinal temperature differences of the solvent are kept as small as possible, since the temperature of the separation column and of the solvent flowing into it are substantially equal, thus avoiding any heat exchange of the solvent inside the separation column, which would have a negative effect on the chromatographic performance.

According to an embodiment of the invention, the heat exchanger capillaries in the first and second heat exchanger devices, respectively, have different lengths over which heat is exchanged, so that a wide range of solvent flow rates can be covered. The inlet and outlet connections of the heat exchangers are arranged such that the shortest possible connection to the separation column is achieved, thus ensuring a minimized dead volume.

It is understood that the underlying concept of the present invention cannot only be used in connection with a pre-column and a separation column, but also in connection with two (possibly different) separation columns arranged in a common housing as described above in connection with FIG. 1. In such an embodiment, the separation columns are preferably connected via a column switching valve. The two columns may have different packing materials and are operated at different temperatures. The purpose of having two columns with different operating parameters (e.g. temperature) is to optimize the separation of a mixture of sample substances in that some of the substances are separated by the first column and some of the substances are separated by the second column, depending on which column provides the best separation characteristics for the specific component. The transfer of substances to a specific column and to a subsequent detector is accomplished by appropriate control of the switching valve arranged between the two columns.

The just described embodiment has the advantage that only a single column housing for both columns operated at different temperatures is required, leading to short connection paths in the apparatus, and thus ensuring a small chromatographic dead volume. Furthermore, the possibility to use different temperatures for the two columns ensures improved separation of the sample components.

The present invention has been described above and implented with reverse phase chromatography, C18 stationary phase material, and aquous/organic solvent as the mobile phases. However, the principle of temperature affecting the distribution of analytes between the mobile and stationary phases applies also in other separation techniques. And hence the present invention is applicable to other modes of chromatography, e.g. normal phase LC, low pressure chromatography, ion exchange chromatography and more. Also the invention applies to multi-dimensional separation techniques, i.e. hyphenated techniques that separate analytes by means of two or more different physico-chemical characteristics. An especially prominent example of this would be 2-dimensional LC with strong cation exchange (SCX) separation in the first dimension followed by reverse phase separation in the second dimension.

Figure 4:
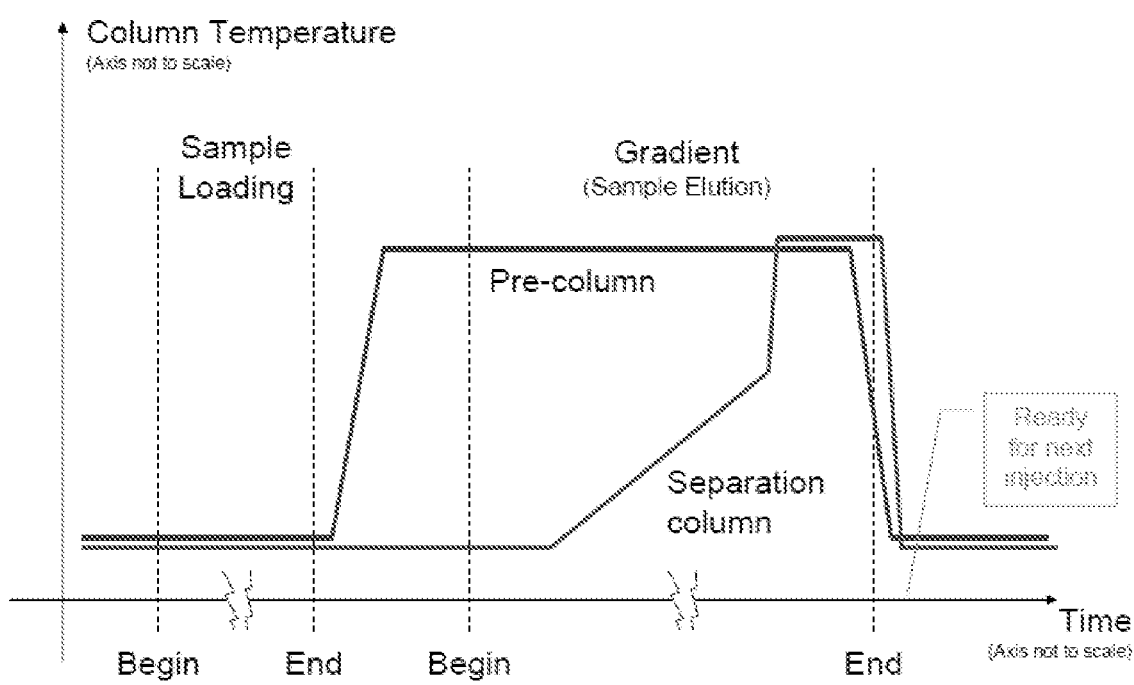
FIG. 4 schematically depicts the gradually increased temperature of the separation column during the gradient elution phase.

The present invention has been described above and implemented with temperature shifts between two levels made very rapidly, relative to the overall chromatographic time-scale. Typically the transition from low to high temperature (or reverse) takes place in ten to 120 seconds for both the pre-column and the separation column. The rapid rise and fall times are indicated also in FIG. 3. However, there are cases in which it is even more beneficial to make the temperature transition in a more gradual manner. In particular, the low operating temperature of the separating column during the gradient elution can lead to peak asymmetry and broadening for some of the more hydrophobic analytes in reverse phase chromatography. Hence the positive TF-effect may be lost again. To mitigate this loss, it is advantageous to gradually increase the temperature of the separation column during the gradient elution phase such as schematically depicted in FIG. 4. Such temperature regulation yields the full DTF effect for both early- and late-eluting compounds.

The present invention has been described and implemented using binary temperature definitions (e.g. high and low) but it is quite conceivable that the desired chromatography enhancing effects be even more pronounced with three or more temperature levels and stepwise transition between these.

The present invention has been described and implemented using a pre-column (also called a trap-column) and a separation column (also called an analytical column) but it should apply equally well to one column separated into different segments only by the temperature control of said segments.

The present invention has been described and implemented using just one pre-column segment and one separating column segment but it should apply equally well to multiple cooling/heating segments that are positioned sequentially along one long column or a number of columns.

The invention claimed is:

1. A method for thermally focusing an analyte passing through a pre-column and a separation column for liquid chromatography, which method comprises the steps:
    operation of the pre-column, during an enrichment phase for enriching a sample in the pre-column, at a first temperature that is lower than ambient temperature and the operating temperature of the separation column and lower than 15° C.;
    heating the pre-column, after completion of the enrichment phase, to a second temperature that is higher than the operating temperature of the separation column and higher than 20° C.;
    eluting the analyte contained in the pre-column to the separation column;
    cooling of the sample to the operating temperature of the separation column;
    eluting the analyte contained in the separation column; and
    thermally desorbing non-eluted sample from the separation column by increasing the temperature to a temperature that is higher than the second temperature of the pre-column;
    wherein the ID of the pre-column is from 150% to 750% of the ID of the separating column.

2. The method according to claim 1, wherein said second temperature that is at least 10° C. higher than the operating temperature of the separation column.

3. The method according to claim 1, wherein the first operating temperature of the separation column is gradually raised to a level that is at least as high as the second temperature of the pre-column during elution in order to also facilitate focused separation of analytes that have a strong interaction with the stationary phase.

4. The method according to claim 1, wherein the first temperature of the pre-column is lower than 5° C., and said second temperature of the pre-column is higher than 45° C.

5. The method according to claim 1, wherein the first temperature of the pre-column is lower than 2° C., and said second temperature of the pre-column is higher than 55° C.

6. The method according to claim 1, wherein said second temperature is at least 20° C. higher than the operating temperature of the separation column.

7. The method according to claim 1, wherein said second temperature is at least 30° C. higher than the operating temperature of the separation column.

8. The method according to claim 1, wherein said second temperature is at least 40° C. higher than the operating temperature of the separation column.

9. The method according to claim 1, wherein the first temperature of the pre column is lower than 10° C., and said second temperature of the pre-column is higher than 35° C.

10. The method according to claim 9, wherein the ID of the pre-column is from 200% to 500% of the ID of the separating column.

* * * * *